United States Patent [19]
Phillips et al.

[11] Patent Number: 5,178,832
[45] Date of Patent: Jan. 12, 1993

[54] SELECTIVE IMMOBILIZATION AND DETECTION OF MYCOTOXINS IN SOLUTION

[75] Inventors: Timothy D. Phillips; Beverly A. Clement; Norman D. Heidelbaugh, all of College Station; William C. Gordon; Linda J. Gordon, both of Bryan, all of Tex.

[73] Assignee: The Texas A&M University System, College Station, Tex.

[21] Appl. No.: 677,361

[22] Filed: Mar. 26, 1991

Related U.S. Application Data

[63] Continuation of Ser. No. 319,844, Mar. 7, 1989, abandoned, which is a continuation of Ser. No. 101,597, Sep. 28, 1987, abandoned.

[51] Int. Cl.$^5$ .................................... C07D 313/00
[52] U.S. Cl. ........................... 422/60; 422/69; 422/88; 436/128; 436/174; 436/178; 435/29
[58] Field of Search ............ 436/128, 178, 174; 435/4, 29; 422/60, 69, 88

[56] References Cited

U.S. PATENT DOCUMENTS

| | | | |
|---|---|---|---|
| 3,954,805 | 5/1976 | Kavka | 549/269 |
| 3,957,825 | 5/1976 | Urry et al. | 549/270 |
| 3,997,568 | 12/1976 | Peters et al. | 549/270 |
| 4,006,265 | 2/1977 | Tamás et al. | 424/130 |
| 4,010,167 | 3/1977 | Young et al. | 549/270 |
| 4,052,414 | 10/1977 | Peters | 549/270 |
| 4,054,515 | 10/1977 | Sawyer, Jr. | 210/27 |
| 4,069,339 | 1/1978 | Ingle et al. | 514/540 |
| 4,181,853 | 1/1980 | Abu-Shumays et al. | 250/304 |
| 4,237,291 | 12/1980 | Grawert et al. | 544/346 |
| 4,239,772 | 12/1980 | Shipchandler | 549/270 |
| 4,690,948 | 9/1987 | Lu | 549/428 |

FOREIGN PATENT DOCUMENTS 0038792 4/1981 European Pat. Off. .
3015537 10/1981 Fed. Rep. of Germany .

OTHER PUBLICATIONS

Hill et al., Determination of Mycotoxins by Gradient High-Performance Liquid Chromatography Using an Alkylphenone Retention Index, Anal. Chem. vol. 56, No. 13, pp. 2576–2579 (1984).

Charles E. Holaday, Rapid Screening Method for Zearalenone in Corn, Wheat and Sorghum, J. Am. Oil Chem. Soc., 491A (1980).

Romer et al., Minicolumn Screening Methods for Detecting Aflatoxin: State of the Art, J. Am. Oil Chem. Soc., vol. 56, pp. 795–797 (1984).

Soares and Rodriguez-Amaya, Screening and Quantitation of Ochratoxin A in Corn, Peanuts, Beans, Rice, and Cassava, J. Assoc. Off. Anal. Chem. vol. 68, No. 6 (1985).

(List continued on next page.)

Primary Examiner—Thi Dang
Attorney, Agent, or Firm—Arnold, White & Durkee

[57] ABSTRACT

It has been discovered that certain minerals, particularly various naturally occurring forms of aluminum oxide, will preferentially bind selective mycotoxins from a mixture of mycotoxins. These adsorbants, when used in various combinations and/or in conjunction with the adsorbants of the prior art, permit the construction of detector tubes which can resolve mycotoxins in solution and provide a semi-quantitative fluorescent determination of their concentration in feed or foodstuff samples. The detector tubes comprise transparent tubes packed with isolated layers of selected minerals. A solvent extract from a sample potentially contaminated with mycotoxins is passed through the column. As the mycotoxin mixture passes through the detector tube and is contacted by the various mineral adsorbants, selected mycotoxins are immobilized on a specific mineral while other mycotoxins and co-extracted organic compounds pass through that layer to be immobilized on subsequent downstream mineral layers. The presence of mycotoxins is determined by examining the developed detector tube under a long wave uv light source.

32 Claims, 2 Drawing Sheets

OTHER PUBLICATIONS

Chemical Abstracts, vol. 96, No. 10, 11, Mar. 1985, (Columbus, Ohio, US), Sano, Akria et al., Fluorodensitometric determination of trichothecene mycotoxins with nicotinamide and 2-acetylpyridine on a silica gel layer, see page 165, abstract 80843x & J. Chromatogr. 1983.

Chemical Abstracts, vol. 105, No. 13, 29 Sep. 1986, (Columbus, Ohio, US), Romer: Use of small charocoal-/alumina cleanup columns in determination of trichothecene mycotoxins in foods and feeds, see p. 563, abstract 11375d, & J. Assoc. Off. Anal. Chem. 1986, 69 (4), 699–670.

DIALOG Informational Systems, File 305, Analytical Abstracts, DIALOG Acc. No. 126079, AAAcc. No. 48-12-F-00056, D. Ehlers: HPLC Determination of patulin in fruit juices: sample preparation with a modified extraction and purification procedure, Lebensmittelchem. Gerichtl. Chem. vol. 40(1), 1986, pp. 2–4, abstract.

DIALOG Informational Systems, File 350, WIP, DIALOG Acc. No. 1988419, WPI Acc. No: 80-83865c/47, Ermakov V et al.: Quantitave determination of mycotoxin in animal tissue, SU, A, 726479 (1980), abstract.

International Search Report, PCT/US 88/03176, Feb. 9, 1989.

SELECTIVE IMMOBILIZATION AND DETECTION OF MYCOTOXINS IN SOLUTION

This is a continuation of copending application Ser. No. 07/319,844 filed on Mar. 7, 1989, now abandoned, which is continuation of Ser. No. 07/101,597, filed on Sep. 28, 1987, now abandoned.

BACKGROUND OF THE INVENTION

1. Field of the Invention

This invention relates to the separation and detection of mycotoxins (e.g. aflatoxins) occurring in grains, nuts, milk, and other foodstuffs. More particularly, the invention concerns the use of various minerals to selectively immobilize certain mycotoxins in a solution comprising one or more mycotoxins and other organic molecules.

2. Description of the Related Art

Mycotoxins are toxic compounds elaborated by fungi. Although the existence of mycotoxins has been known for many years, they have been studied less intensively than bacterial toxins in foods. Interest in the effects of mycotoxins was renewed in recent years after the discovery that aflatoxins were the causative agents in turkey X disease which killed thousands of turkeys in England in 1960.

Aflatoxins

Aflatoxins are fluorescent toxic factors elaborated by the common mold *Aspergillus flavus,* among others. Originally two families were isolated; they were named aflatoxin Band G, because they exhibited blue and green fluorescence, respectively. More recently, at least eight compounds have been shown to belong to the aflatoxin group. The toxins have similar structures and form a unique group of highly oxygenated, naturally occurring heterocyclic compounds that fluoresce upon exposure to ultraviolet light. The homologs which comprise the aflatoxins commonly designated $B_1$, $B_2$, $G_1$, and $G_2$ have the following chemical structures:

G1

B1

G2

-continued

B2

Ochratoxins

Members of the ochratoxin group of mycotoxins (i.e., ochratoxins A and B and corresponding methyl and ethyl esters and 4-hydroxyochratoxin A) are structurally related derivatives of 3,4-dihydro-3-methylisocoumarin linked by an amide bond to L-beta-phenylalanine at the 7-carboxy group. These chemicals can be produced by several species of the fungal genera Aspergillus and Penicillium. Ochratoxin A has been reported to occur as a natural contaminant in a variety of food and feedstuffs (e.g., corn, wheat, barley, dried beans, sorghum, moldy peanuts, mixed feed, green coffee beans, etc.) as well as residues in liver, kidneys and adipose tissue of pigs. The toxicity of ochratoxin A has been well documented in numerous experimental animals. Although this mycotoxin has drawn the greatest attention for its potent nephrotoxicity, it is also capable of eliciting other toxic effects including teratogenesis.

Ochratoxin A, a toxic metabolite of *Aspergillus ochraceus*, has the following chemical structure:

Ochratoxin A, when present in combination with aflatoxins, may bias the determination of aflatoxins when the minicolumn analytical test methods of the prior art are employed. The present invention eliminates this bias by providing a means to resolve a mixture of mycotoxins comprising aflatoxins and ochratoxin A.

Trichothecenes

Trichothecenes such as deoxynivalenol (DON) and related sesquiterpene alcohols are another very important class of mycotoxins due to their toxicity and frequent occurrence in grains. They generally have the carbon skeleton:

The trichothecenes are a group of some 50 biologically active sesquiterpenes produced by various species of fungi. They are chemically characterized by a 12,13-epoxy-trichothec-9-ene ring system. These compounds have been implicated as causal agents in both human and animal poisonings. As a group, the trichothecenes exhibit a wide spectrum of toxicity. Clinically, the ingestion of trichothecenes can result in vomiting, diarrhea, anorexia, ataxia, hematuria, leukocytosis and severe leukopenia, inflammation of the GI tract, degeneration of nerve cells, degeneration of cardiac muscle, and lesions of the lymph nodes, testes and thymus. Topical contact can result in several dermal necrosis. The trichothecenes have been strongly linked to the etiopathogenesis of natural intoxications (i.e., moldy corn toxicosis of cattle, swine and poultry in the U.S.; Akakabi-Byo disease in Japan; Stachydotryo-toxicosis and alimentary toxic aleukia in the U.S.S.R.; and dendrodochiotoxicosis).

The minicolumn techniques of the prior art do not have the ability to separate trichothecenes from aflatoxins or even detect them on the same column in one step.

Zearalenone

Zearalenone, ([6-(10-Hydroxy-6-oxo-trans-1-undecenyl)-beta-resorcyclic acid lactone]), is a commonly occurring mycotoxin produced by *Fusarium roseum* (F. Gramineaum) and other Fusarium species on corn, sorghum, barley, wheat and other cereals. There have been numerous reports of zearalenone contamination of corn and commercial preparations of mixed feeds. In the case of wet-milled products from corn contaminated with zearalenone, it has been demonstrated that this mycotoxin becomes concentrated in those fractions generally used for animal feeds. When fed to animals (particularly swine), zearalenone causes a condition commonly referred to as hyperestrogenism. In swine, this syndrome involves primarily the genital system (e.g., swollen and edematous vulva, rectal and vaginal prolapse, enlarged uterus in the female pig, and a feminizing effect with atropy of the testes and enlargement of the mammary glands in the young male). Besides the estrogenic symptoms, other clinical signs of zearalenone intoxication can include: diarrhea, emesis, refusal of feed, loss of weight and hemorrhage.

Steriomatocystin

Sterigmatocystin, (3a,12c-Dihydro-8-hydroxy-6-methoxyfuro[3,2':4,5]furo[3,2-c]xanthen-7-one), is a mycotoxin produced by a variety of Aspergillus fungi and is also produced as an intermediate product in the biosynthesis of aflatoxins by *A. parasiticus* and *A. flavus* in foods and feeds. This mycotoxin produces liver and kidney damage in experimental animals. In monkeys, sterigmatocystin is reported to cause chronic hepatitis and hyperplasia. It has been hypothesized that like aflatoxins, sterigmatocystin is involved in the etiology of chronic liver disease of humans in Africa.

Patulin

Patulin (4-Hydroxy-4H-furo[3,2-c]pyran-2(6H)-one) is a toxic lactone produced by several fungi belonging to the genera Aspergillus and Penicillium. *Penicillium expansum* is the cause of common storage rot of apples and can result in as much as 17 mg of patulin in a single rotten apple. Of practical interest to the food industry is the fact that patulin is stable in apple juice and grape juice and thus occurs frequently as a contaminant of these foods. Patulin has been reported to be moderately toxic to animals and potentially carcinogenic in the male rat. In humans, oral administration of patulin has resulted in nausea and stomach irritation. Applications of 1% patulin to the skin has caused edema. Additionally, patulin has been shown to be cytotoxic (inhibiting cell division) and toxic to plants, fungi, yeasts, bacteria, protozoa and bacterial viruses.

Citrinin

Citrinin, [(3R-trans)-4,6-Dihydro-8-hydroxy-3,4,5-trimethyl-6-oxo-3H-2-benzopyran-7-carboxylic acid], is produced by a variety of Penicillium and Aspergillus fungi. It has been reported to co-occur with ochratoxin A and may play a role in field outbreaks of porcine nephropathy. The renal toxicity of citrinin in swine has been characterized by lesions and desquamation of renal epithelial cells of the proximal convoluted tubules, dilation of tubules, thickening of basal membranes and proliferation of cells in the interstitium. Citrinin has been shown to produce irritation of the nasal passages in humans following inhalation. In addition to its potent nephrotoxicity, citrinin has a depressant effect on respiration and the cardiovascular system in experimental animals.

Ergots

Ergot alkaloids (the most potent of the ergots) are principally metabolites of a group of closely related ergot fungi of the genus Claviceps or Sphacelia. Chemically, these alkaloids are amide or cyclic tripeptide derivatives of lysergic acid and can occur naturally only in the sclerotia produced during parasitism of grass and cereal host plants. The toxicity of ergot alkaloids results from their wide range of pharmacological activities involving the central nervous system, antagonism toward adrenaline and 5-hydroxytryptamine, and peripheral action expressed through the stimulation of smooth muscle (e.g., uterus, arteriole walls, or sphincter pupillae). Poisoning, due to ingestion of ergo talkaloid mycotoxins, has been reported in humans, cattle, sheep, horses, swine and poultry.

Although other mycotoxins have been and are being discovered, the aflatoxins retain a position of major importance because of their high toxicity and their common natural occurrence in such foods as cereal grains, oil-seeds, and oilseed meals stored under adverse conditions. The ability of aflatoxins to cause liver cancer has probably been the key factor in worldwide concern over their presence in foods and feeds. Although the effects of aflatoxins on humans are not clear at present, the mycotoxins are highly potent carcinogens to a number of animals and should be regarded as potentially hazardous to humans. Many agricultural commodities support the production of aflatoxins if conditions are favorable for the growth of A. flavus or other toxin-producing molds.

Generally, most aflatoxin production occurs during the harvest period after cereals, oilseeds or nuts have begun to dry but before they attain the moisture level best suited for storage. Storage of the foodstuffs under proper temperature and humidity conditions will prevent further contamination. Thus, it is recognized that one very effective step to ensure a wholesome product is to divert from edible use any contaminated lots as early in the food processing chain as possible. Accordingly, a need exists for simple, rapid, and convenient tests for mycotoxin contamination for use in the field. More especially, a need exists for test devices and procedures capable of resolving and separately detecting specific mycotoxins in a mixture comprising other mycotoxins and co-extracted organic compounds.

Chromatographic procedures for aflatoxins using classical minicolumns have been described by a number of researchers. These techniques are reputed to be suitable for the field analysis of corn and peanuts. See, e.g., Holaday, C. E., "A Rapid Screening Method for the Aflatoxins and Ochratoxin A," J. Am. Oil Chem. Soc. 53:603 (1976); Holaday, C. E., "Rapid Screening Method for Zearalenone in Corn, Wheat and Sorghum," J. Am. Oil Chem. Soc. 491A (June 1980); Shotwell, O. L. and C. E. Holaday, "Minicolumn Detection Methods for Aflatoxin in Raw Peanuts: Collaborative Study," J. Assoc. Off. Anal. Chem. 64:674 (1981); Holaday, C., "Rapid Screening Method for Aflatoxin $M_1$ in Milk," J. Assoc. Off. Anal. Chem. 64:1064 (1981); Holaday, C. E., "Minicolumn Chromatography: State of the Art," J. Am. Oil Chem. Soc. 931A (December 1981).

In general, two methods of detecting aflatoxins using minicolumns are described in the prior art. In one, silica gel is the primary packing of the minicolumn. The minicolumn (or "millicolumn") is developed in a chloroform-methanol extract of a grain or oilseed sample. If aflatoxin is present, a blue fluorescent band at the lower end of the column is observed when the column is exposed to long-wave ultraviolet radiation. [See, e.g., Holaday, J. Am. Oil Chem. Soc. 45:680 (1968)]. The other general method employs Florisil ® brand activated magnesium silicate (see U.S. Pat. No. 2,393,625) to bind the aflatoxins in the column. Extracts of the sample are purified and then applied to the column in a chloroformacetone solution. The column is then filled with chloroform and allowed to drain. If aflatoxins are present above the detection limit, they will be detected as a fluorescent glow in the Florisil ® layer when examined under longwave uv light. [See, e.g., Velasco, J. Am. Oil Chem. Soc. 49:141 (1972)]

Holaday has additionally described a screening method for the aflatoxins and ochratoxin A using minicolumns packed with Florisil ®. Two columns are used. The aflatoxin minicolumn has a layer of alumina upstream from the Florisil ® layer. The ochratoxin A minicolumn is packed only with Florisil ®. The sample is blended in a methanol-water solution; treated with an aqueous solution of zinc sulfate and phosphotungstic acid; and extracted with benzene before being applied to the columns. The aflatoxin column is developed by pulling a hexane-acetone solution through it. Methanol is used to develop the column for ochratoxin A. Both analytes are detected by visual observation of the mycotoxins' fluorescence under uv light. [Holaday, J. Am. Oil Chem. Soc. 53:603 (1976)]

There are other types of chromatography which will perform the same function as the invention disclosed herein—the separation and detection of various mycotoxins. These include analytical methods employing high performance liquid chromatography (HPLC), thin-layer chromatography (TLC), gas-liquid chromatography (GLC), and gas chromatography/mass spectrometry (GC/MS). Unfortunately, these techniques are not well suited for performing analyses in the field inasmuch as they require complex instruments and a relatively high degree of skill on the part of the person performing the analysis.

SUMMARY OF THE INVENTION

It has been discovered that certain minerals, particularly various naturally occurring forms of aluminum oxide ($Al_2O_3$), will preferentially bind selective mycotoxins in a mixture of mycotoxins. These adsorbants, when used in various combinations and/or in conjunction with the adsorbants of the prior art, permit the construction of devices which can resolve mycotoxins in solution and provide a semi-quantitative fluorescent determination of their concentration in foodstuff samples. The devices of the present invention are easy to fabricate using readily available, relatively inexpensive materials and the test methods which employ these devices are rapid and easily performed in the field.

The test devices of the present invention comprise transparent tubes packed with isolated layers of selected minerals. In use, a solvent extract from a sample potentially contaminated with mycotoxins is passed through the detector tube or is transported through the tube by a different solvent or solvent mixture. As the mycotoxin mixture passes through the device and is contacted by the various mineral adsorbants, selected mycotoxins are immobilized on a specific mineral while other mycotoxins pass through that layer to be immobilized on subsequent downstream mineral layers. If the mycotoxins for which the device is specific are present in the sample above the detection limit they will appear as fluorescent bands near the top of the mineral layers which are selective for those particular mycotoxins when the developed detector tube is exposed to uv radiation. For some mycotoxins, it is necessary to heat the test device to convert the mycotoxin to a fluorescent product. Specially treated minerals may be employed to facilitate this conversion.

Semi-quantitative results may be obtained by comparing the fluorescence emission intensity of the mycotoxins immobilized in the test device to that of standard test devices or other fluorescent controls.

DETAILED DESCRIPTION

The present invention employs adsorbants having structure-selective affinities to various mycotoxins commonly occurring in agricultural commodities and foodstuffs. The selective adsorption properties of these materials enables the construction of a test device which can immobilize selected mycotoxins at certain physical locations in the test device thereby permitting the resolution and subsequent detection of mycotoxins extracted from samples of grain, oilseeds, and the like.

This immobilization phenomenon also enables one to physically separate the mycotoxin(s) of interest from interfering compounds. Interfering compound are most commonly other fluorescent species. However, substances which quench the fluorescence of the analyte and/or block the exciting uv radiation on the emitted fluorescence of the analyte in the visible portion of the spectrum are also considered interfering compounds for the purposes of this disclosure.

For the purposes of this disclosure, to "bind" or "immobilize" the mycotoxin analyte(s) or interfering compounds means that the substance is not appreciably eluted from the selective adsorbant by the sample solution or wash solvent(s). It should be appreciated that this differs fundamentally from chromatographic methods of analysis. Chromatography is based on the separation which obtains when substances having different affinities for the stationary phase are dissolved in a mobile phase and passed through a bed of or across a layer of the stationary phase. In column chromatography, the compounds of interest are typically detected (or collected) as they exit the column, having been eluted by the mobile phase. In contrast, the affinities of the present invention are such that for all practical purposes, no significant elution of the mycotoxin from its selective adsorbant takes place when the recommended types and quantities of dissolving solvents and transporting (or "wash") solvents are used and detection takes place with the mycotoxin within the test device.

The minerals and the mycotoxins which they selectively bind or otherwise immobilize are: Florisil ® for aflatoxins; bayerite for ochratoxin A, sterigmatocystin, and citrinin; pseudoboehmite for ochratoxin A, zearalenone, and citrinin; alumina for zearalenone, deoxynivalenol, patulin, sterigmatocystin and ergots; and, silica gel for patulin, sterigmatocystin and ergots.

For binding and immobilizing certain mycotoxins, the following minerals have been found to be effective: for ochratoxin A, pseudoboehmite and other aluminum oxides including bayerite, gibbsite, boehmite, bauxite and alumina (activity grade IV or V); for zearalenone, neutral alumina and other aluminum oxides (of activity grade I or II), including acidic or basic alumina, bayerite, bauxite, boehmite, pseudoboehmite, and gibbsite; for patulin, acidic alumina and other aluminum oxides including bayerite, gibbsite, boehmite, pseudoboehmite, and bauxite, and silica gel; for sterigmatocystin, neutral alumina, grade I, including boehmite, pseudoboehmite, bauxite, gibbsite, and bayerite; for deoxynivalenol, neutral alumina and other aluminum oxides including bayerite, boehmite, pseudoboehmite, bauxite, gibbsite, and acidic alumina, and silica gel; for citrinin, bayerite, pseudoboehmite, bauxite, gibbsite, boehmite, and alumina; and, for ergots, alumina and silica gel.

Florisil ®, a hard, porous, granular substance, is a brand of activated magnesium silicate typically used in vitamin analysis, chromatography, and antibiotic processing [see Simons, U.S. Pat. No. 2,393,625 (1946 to Floridin)]. As noted above, its use in selectively binding aflatoxins from solutions comprising aflatoxins has been described in the literature.

Bayerite, pseudoboehmite, and alumina are all forms of aluminum oxide ($Al_2O_3$). Aluminum oxide (alumina) occurs abundantly in nature, most often as impure hydroxides which are the essential constituents of bauxites and laterites. The numerous purer grades of alumina manufactured from these ores are major chemical products.

The nomenclature used for the various crystallized hydrates of alumina has not been completely standardized and these materials are differently named in various countries. An effort toward world uniformity has been made in recent years. Table 1 provides a summary of some of the more commonly used names and synonyms.

TABLE 1

| Nomenclature of Crystallized Hydrates of Alumina | | | |
|---|---|---|---|
| Composition | Alcoa | European symposium | CAS Registry No. |
| $Al(OH)_3$ | α-alumina trihydrate | hydrargillite or gibbsite | [14762-49-3] |
|  | β-alumina trihydrate | bayerite | [20257-20-9] and [12252-72-1] |
|  | new β-trihydrate | nordstrandite | [13840-05-6] |
| AlOOH | α-alumina monohydrate | boehmite | [1318-23-6] |
|  | β-alumina monohydrate | diaspore | [14457-84-2] |

The structural properties of gibbsite, bayersite, and boehmite are set out in Table 2.

TABLE 2

| Structural Properties of Oxides and Hydroxides | | | | |
|---|---|---|---|---|
|  | Minerals | | | |
|  | Gibbsite | Gibbsite | Bayerite | Boehmite |
| Formula | $Al(OH)_3$ | $Al(OH)_3$ | $Al(OH)_3$ | AlOOH |
| Crystal system | Monoclinic | Triclinic | Monoclinic | Orthorhombic |
| Space group | $C_{2h}^5$ |  | $C_{2h}^5$ | $D_{2h}^{17}$ |
| Molecules per unit cell | 4 | 16 | 2 | 2 |
| Unit Axis Length, nm | | | | |
| a | 0.868 | 1.733 | 0.506 | 0.286 |
| b | 0.507 | 1.008 | 0.867 | 1.222 |
| c | 0.972 | 0.973 | 0.471 | 0.370 |
| Angle | 94°34' | 94°10' 92°08' 90°0' | 90°16' |  |
| Density, g/cm³ | 2.42 |  | 2.53 | 3.01 |

Boehmite is a grayish, brownish, or reddish orthorhombic mineral: AlO(OH)—i.e., a mineral consisting of an orthorhombic form of aluminum oxide and hydroxide. It is a major constituent of some bauxites and it represents the gamma phase dimorphous with diaspore. Diaspore, also known as β-alumina monohydrate, is a well-crystallized modification of AlOOH which occurs in certain high alumina clays in Missouri and Pennsylvania. It is a major consitutent of Greek, Rumanian, and Russian bauxites.

Pseudoboehmite is gelatinous boehmite. Alumina gels are generally prepared from solutions of $Al_2(SO_4)_3$ and $NH_3$, or from $NaAlO_2$ and an acid, or from $NaAlO_2$, and $Al_2(So_4)_3$ and produce corresponding by-product salts. The precipitate, after being washed, is thoroughly drained to form a cake which embodies 8-20% $Al_2O_3$. The x-ray diffraction pattern of the alumina at this point is pseudoboehmite [see B. R. Baker and R. M. Pearson, J. Catal. 33, 265 (1974)]. This cake may be dried directly and broken up, or it can be extruded in the form of cylinders. An alternative is to reslurry and spray-dry the washed cake, which produces spherical particles of about 5 nm in diameter.

Alumina suitable for chromatographic adsorption is typically prepared from carefully screened aluminum hydroxide having a particle size which will pack easily in a column without obstructing the seepage of liquids (typical sieve analysis: all through 150 mesh, 40% on 200 mesh, 40% on 325 mesh). It is believed that the average particle size is probably about 7 microns. The aluminum hydroxide is dehydrated and calcined at about 900° C. in a $CO_2$ stream which tends to coat the individual $Al_2O_3$ particles with a thin layer of aluminum oxycarbonate approximating the formula $[Al_2(OH)_5]_2CO_3.H_2O$. Water content and alkalinity are then adjusted by washing with dilute acids.

Silica gel is precipitated silicic acid in the form of lustrous granules. It is a colloidal silica resembling coarse white sand in appearance but possessing many fine pores and is therefore extremely adsorbent.

Figure 1:
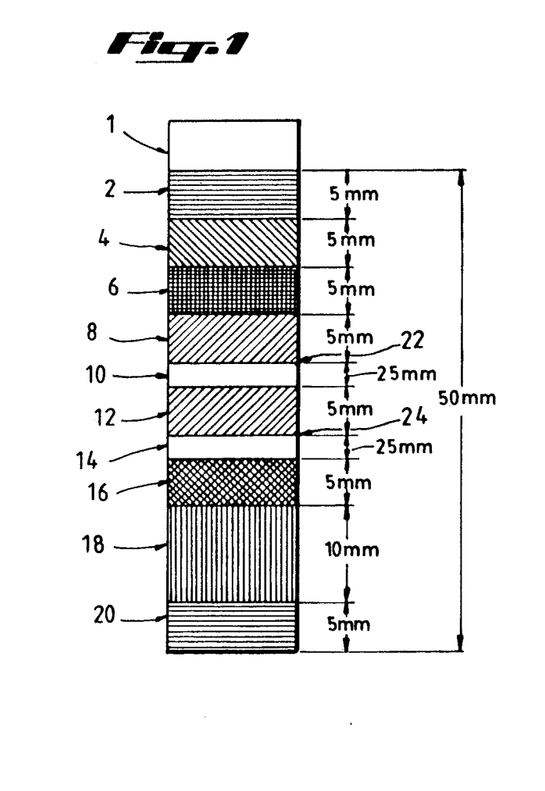
FIG. 1 depicts in cross section a portion of a test device embodying the present invention. The particular device illustrated permits the immobilization and detection of ochratoxin A and aflatoxins.

The novel use of these various minerals (and others) to selectively bind and immobilize specific mycotoxins in solution, thereby permitting their ready detection, can best be understood by reference to the following examples. The fabrication and use of various representative test devices ("detector tubes") which embody the present invention are disclosed in the examples below. However, it should be appreciated by those skilled in this art that these examples are merely illustrative of the invention and a great variety of embodiments are possible which employ various combinations of these selective adsorbants and others depending on the various mycotoxins or combinations of mycotoxins for which analysis is desired.

EXAMPLE 1

The packed portion of a detector tube for the resolution and detection of aflatoxins and ochratoxin A which embodies the present invention is depicted in cross section in FIG. 1. The positions of the selective adsorbants (reactive interfaces) having structure-selective affinities to mycotoxins are shown along with the locations of various packing materials used to separate and/or support the adsorbants and to precondition the sample solution and transporting solvent(s). Also shown in FIG. 1 are the locations of the analytes after the detector tube has been developed. The selective adsorption capabilities of the detector tube packings permit the resolution and subsequent fluorescent detection of aflatoxins and ochratoxin A extracted from samples of grain, oilseeds, and the like.

The tube containing the selective adsorbants and associated packings is preferably about 4 mm OD and has the other approximate dimensions shown in the figure. To permit fluorescent detection of the mycotoxins bound to the adsorbants in the detector tube, the tube itself must be substantially transparent to both the exciting uv radiation and the emitted fluorescence in the visible portion of the spectrum and non-fluorescent. Quartz is especially preferred but ordinary borosilicate or sodalime glass will suffice as will polycarbonate, acrylic, and other transparent plastics.

In FIG. 1 detector tube 1 is shown with a number of additional, optional packings which improve the separation and detection of mycotoxins. Layer 2, the top layer in the detector tube shown, is sand. Its purpose is to minimize column loading disturbances when the sample solution is applied to the detector tube. Layer 4 is anhydrous sodium sulfate. As the sample solution or transporting solvent passes through this layer any water in the solvent is absorbed by the sodium sulfate via hydration. It is not necessary, however, that the solvents be dried in this manner or even dried at all.

Layer 6 is activated charcoal. It acts to remove contaminants from the sample solution, particularly pigments which may have been extracted along with the analytes. Layer 8 is Celite® diatomaceous earth (infusorial earth). It contains the charcoal layer and separates it from the ochratoxin A selective layer.

Layer 10 preferably comprises bayerite. As discussed above, bayerite is a crystallized aluminum trihydroxide. Bayerite selectively adsorbs ochratoxin A from the sample solution and binds it, immobilizing this mycotoxin at position 22 in FIG. 1. If ochratoxin A is present in the sample in sufficient quantity to permit visual observation of its fluorescence, a bright blue band at position 22 will be seen when the detector tube is exposed to longwave uv radiation. Aflatoxins are not bound by the bayerite layer and they are transported to the downstream layers in the detector tube. Any other selective adsorbant which binds ochratoxin A but not aflatoxins could be substituted for bayerite in this layer. Layer 12 is Celite® diatomaceous earth or sand. It separates the mycotoxin selective layers in the detector tube.

Layer 14 preferably comprises Florisil® activated magnesium silicate. Aflatoxins in the sample are bound by the Florisil® and immobilized. They can subsequently be detected as a bright blue fluorescent band at position 24 in the detector tube when the tube is exposed to longwave uv light (emission maximum at approximately 365 nm). Other selective adsorbants which bind aflatoxins can be employed in this layer. In particular, silica gel can be used for this purpose (see, e.g., Holaday, JAOCS 45:680 (1968)).

It is important that the bayerite layer (or other ochratoxin A selective adsorbant) be upstream from the layer used to bind aflatoxins if the aflatoxin adsorbant also binds ochratoxin A (as is the case with Florisil®). An "upstream" packing in the detector tube is contacted by the sample solution prior to a "downstream" packing as the sample solution passes through the detector tube in the intended direction. If the positions of the selective adsorbants in the detector tube were reversed with respect to the flow of sample solution or transporting solvent, no separation would obtain inasmuch as both the ochratoxin A and the aflatoxins would be bound on the Florisil® layer and the sample solution would be essentially free of any ochratoxin A by the time it contacted the bayerite layer.

Layer 16 supports the Florisil® layer and forms an "optical barrier" which prevents the diffusion of the emitted fluorescence from the excited aflatoxins into layer 16 thereby enhancing the visible detection of that analyte. Any material which satisfies this criterion and is porous but insoluble in the sample solution and transporting solvents could be used. Celite has been found to work well in this application. Other materials considered suitable include glass wool, silicates, salts (if insoluble in the solvents employed), carbon, sulfur, iron filings, various plastics, aluminosilicates, cellulose fiber, sand, and the like, and mixtures of such materials.

The packings of the detector tube shown are supported on a layer of alumina, 18. Glass wool plug or frit 20 holds the packings in the detector tube. It should be noted that the only layers which are essential to the practice of the invention are the adsorbants which are selective for ochratoxin A and aflatoxins—in the illustrated embodiment, bayerite (layer 10) and Florisil ® (layer 14), respectively. The other layers employed in this embodiment serve to support and isolate the active layers (selective adsorbants) or to precondition the sample solution and/or transporting solvent(s).

The detector tube for the selective adsorption of mycotoxins disclosed above allows extracts from grain samples and the like to be analyzed in the field for aflatoxins and ochratoxin A. The analysis is accomplished by concentrating the extract from the sample and dissolving the residue in a known volume of an appropriate solvent such as methanol. Suitable extraction procedures are well-known in the art. In general, any of the AOAC-sanctioned procedures for extractions of such samples may be employed. An aliquot of the extract is loaded on the top of the detector tube and transported with a developing solvent (e.g., methanol). Positive pressure may be applied to the top of the detector tube to decrease the elution period.

After development, the detector tube is exposed to longwave uv radiation. Longwave uv radiation is ultraviolet energy in the wavelength region from about 320 to 400 nanometers. This region is also known as the near ultraviolet or black light. Fluorescent and mercury lamps can be filtered so that visible energy is absorbed and their emission is primarily in this portion of the spectrum. Such sources typically have an emission maximum at about 365 nm. A mercury arc lamp has a prominent line at 365.4 nm. If present in the extract above the detection limit, ochratoxin A will be detected as a bright blue fluorescent band near the upper end (upstream end) of the ochratoxin-selective layer (the bayerite layer in the illustrated embodiment). Similarly, aflatoxins will be detected as a blue fluorescent band near the upstream limit of the aflatoxin-selective layer (Florisil ® in the illustrated embodiment).

A semi-quantitative determination may be made by constructing a "mycotoxin standard control card" having fluorescent bands of different intensities corresponding to a range of mycotoxin concentrations in the sample. A side-by-side comparison under the same uv light source of the developed detector tube and the control card would enable an estimation to be made of the ochratoxin A and aflatoxin concentrations in the sample. This technique has the particular advantage of obviating the need for actual mycotoxin standards which would be hazardous to ship and use in the field.

More quantitative results can be obtained by instrumental fluorometry, the intensity of fluorescence from the analytes in the developed detector tube being measured in a fluorometer. The detector tubes of the invention are stable, even after developing. Fluorescence from the mycotoxin analytes has been observed in detector tubes developed more than one year prior to the observation.

Samples of both "spiked" and naturally contaminated grain sorghum, peanuts, corn and wheat were homogenized and partitioned by polarity with aqueous acetone (60% v/v acetone) or acetonitrile and hexane followed by extraction of the aqueous layer with chloroform. The chloroform extracts were concentrated under dry nitrogen and the resulting residue redissolved in a known volume of ethanol prior to analysis. Aliquots ranging from 20 to 100 microliters of this extract were loaded on the top of the detector tube and transported (i.e., moved sequentially through the various packing layers) with a 1:1 mixture of chloroform and methanol. Positive pressure was applied to the top of the detector tube using a pipette bulb attached to the top of the tube during the development period (about 15-60 seconds).

The developed detector tube was visualized under a uv lamp (365 nm). Ochratoxin A was detected as a bright blue fluorescent band in the bayerite layer. The aflatoxins were concentrated as a tight band at the interface of the Celite ® and Florisil ® layers and were detected by their bright blue fluorescence.

After use the detector tubes can be decontaminated by pushing an oxidizing agent through them. Household bleach (aqueous sodium hypochlorite) can be used for this purpose. Alternatively, if the housing of the detector tube is acrylic or polycarbonate plastic, the device can be disposed of by incineration.

The detector tube and method described above will prove useful as a regulatory tool to monitor aflatoxin contamination in agricultural commodities, prepared foods and mixed feeds at buying locations, field installations, processing lines, grain elevators, feed lots, and the like. It can facilitate the rapid differential diagnosis of mycotoxicoses in animals (by testing body fluids or tissue extracts, particularly those of the liver and kidney) and perform presumptive field analyses for aflatoxins and ochratoxin A.

The above-disclosed embodiment of the invention has the unique features of the ability to detect both aflatoxin and ochratoxin A in one step using the same detector tube and the ability to separate aflatoxin from ochratoxin A so that this mycotoxin (when present in combination with aflatoxin) will not generate false positive results for aflatoxin.

Among the advantages which may be realized by the use of detector tubes which embody the present invention are: speed of analysis (15 to 20 minutes for semiquantitative results); ease of use (technical expertise and a source of vacuum are not required, the force of gravity being sufficient to develop the detector); sensitivity (part-perbillion level detections possible); economy (minimal production costs and no antibodies or enzymes required as they are for many competing techniques such as ELISA); stability (no refrigeration required, detector tube packings are non-thermolabile); and flexibility (the detector tube and associated method can provide a go/no-go field test or be used as a semiquantitative, pre-screening test for more quantitative instrumental methods such as HPLC).

EXAMPLE 2

A detector tube and assay method for ochratoxin A, zearalenone, and aflatoxins which embodies the present invention utilizes pseudoboehmite, alumina, and Florisil ® in combination to separate, immobilize and thereby fluorescently detect ochratoxin A, zearalenone, and aflatoxins, respectively.

Figure 2:
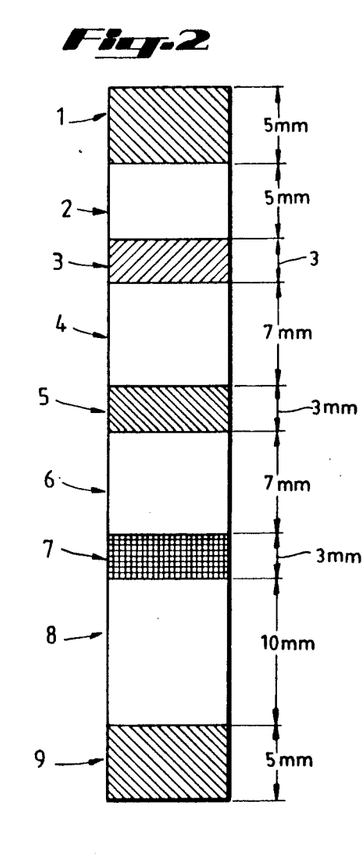
FIG. 2 depicts in cross-section a portion of a test device which embodies the present invention. The device illustrated may be used to detect zearalenone, ochratoxin A, and aflatoxins.

The packed portion of the detector tube is shown in cross section in FIG. 2. The tube which houses and contains the selective adsorbants is preferably about 5 mm ID. The preferred approximate thicknesses of the various packings of the detector tube are indicated in the figure. Preferred materials for the detector tube housing are the same as those discussed in Example 1, above.

In the detector tube shown in FIG. 2, nine layers of various packings have been used to accomplish the specific resolution of the three analytes (ochratoxin A, zearalenone, and aflatoxins). Materials in addition to the selective chemisorbants are employed to improve the separation and detection. In the detector tube shown, layers 1 and 9 are cotton which act to maintain the physical integrity of the other layers during use, handling and storage. Other materials considered suitable for this purpose include glass wool, filter paper and other cellulosic materials, plastic frits, and the like. Layer 1 functions additionally to filter out particulates in the sample solution.

Layers 2, 4, 6, and 8 are preferably sand. They function to physically separate the selective chemisorbants thereby enhancing the differentiation of the fluorescent emission of the mycotoxins immobilized in the chemisorbant layers. Layer 2 performs the additional function of filtering out or adsorbing interfering materials from the sample solution as it passes through the column before contacting the selective chemisorbants. Any material which accomplishes these functions and is porous but insoluble in the sample solution and solvent(s) used to transport the sample through the detector tube could be used.

Layer 3 preferably comprises pseudoboehmite. Pseudoboehmite selectively adsorbs ochratoxins from the liquid sample solution and binds them, immobilizing ochratoxin A at or near the upstream end of layer 3. If ochratoxin A is present in the sample in sufficient quantity to permit visual detection of its fluorescence, a bright blue band in layer 3 will be seen when the detector tube is exposed to longwave uv radiation (365 nm). Zearalenone and aflatoxins are not bound by this chemisorbant and thus these mycotoxins pass through to the downstream layers in the detector tube. Any other chemisorbant which binds ochratoxin A and not zearalenone or aflatoxins could be substituted for pseudoboehmite in this layer.

Layer 5 comprises neutral alumina (Brockmann and Schodder). This chemisorbant selectively adsorbs zearalenone from the sample solution while allowing aflatoxins to pass through to downstream layers. If zearalenone is present in the sample in sufficient quantity to permit visual observations of its fluorescence, a bright blue band in layer 5 will be seen when the detector tube is examined under longwave uv radiation. Any other absorbant which binds zearalenone and not aflatoxins could be substituted for neutral alumina in this layer.

Layer 7 preferably comprises Florisil® brand activated magnesium silicate. It selectively absorbs aflatoxins in the sample solution but allows other classes of organic compounds which might be present in the sample solution and constitute an interfering substance to pass through. If aflatoxin is present in the sample in sufficient quantity to permit visual observation of its fluorescence, a bright blue band at layer 7 will be seen when the detector tube is exposed to longwave uv radiation.

It is important that the pseudoboehmite-selective adsorbant be upstream from the chemisorbants used to bind zearalenone and aflatoxin if the ochratoxin A is capable of binding where zearalenone or aflatoxin bind (as is the case where ochratoxin binds to neutral alumina and to Florisil®). Likewise, if zearalenone binds to the aflatoxin adsorbant (which it does if Florisil® is used), the zearalenone adsorbant must be upstream from the aflatoxin adsorbant. Therefore, if the selective adsorbants were arranged in any different relative order, separation of the analytes would not obtain upon development of the detector tube with a sample solution containing these three analytes.

It should be appreciated that the only layers which are essential to the analysis are the adsorbants which are selective for ochratoxins, zearalenone and aflatoxins—in the illustrated case, pseudoboehmite, neutral alumina, and Florisil®, respectively. The other layers employed in the detector tube illustrated serve to support and isolate the selective adsorbants or to precondition the sample solution and/or the transporting solvent (e.g., by removing particulates).

The detector tube described above permits the analysis of the chemicals indicated which are mold-elaborated toxins (mycotoxins) often present in grains, nuts and other feed and food commodities. The analysis may be accomplished by dissolving the mycotoxins in a known volume of an organic solvent having the property of being able to simultaneously dissolve ochratoxin A, zearalenone and aflatoxins as possessing the appropriate characteristics which allow the mycotoxins to bind to the appropriate adsorbants as the sample solution is passed through the detector tube. Examples of appropriate solvents are benzene or toluene saturated with a solution of 40% methanol in water (v/v), or acetone/water mixtures.

The sample is applied to the top of the detector tube (e.g., one mL or less) and is allowed to flow through the device. The detector tube is further developed by adding a volume (e.g., one mL) of a wash or "transporting" solvent which is also allowed to flow through the detector tube. Differential pressure may be applied to the detector tube to increase the rate of flow. Solvents with the same general characteristics as the solvents used to dissolve the sample as well as those solvents themselves may be used as wash solvents. Other appropriate wash solvents are: toluene/acetone (9:1); toluene/-chloroform/acetone (95:20:5); chloroform/acetone (9:1); and, ethyl acetate/methanol (4:1).

Following development (i.e., passage of the sample solution through the detector tube), the device is examined under an ultraviolet lamp preferably having an emission maximum at approximately 365 nm. If present in the extract above the detection limit, ochratoxin A will be detected as a bright blue fluorescent band in the ochratoxin selective layer (pseudoboehmite in the illustrated device), aflatoxins will appear as a blue fluorescent band in the aflatoxin-selective layer (here, Florisil®), and zearalenone will similarly be apparent as a blue fluorescent band in the layer which selectively adsorbs resorcilinic acid derivatives (here, alumina).

The intensity of the fluorescence emission in any of the mycotoxin-selective layers in the sample detector tube may be compared to the fluorescence of known quantities of the various mycotoxins applied to similar detector tubes in the same manner and thus representing "reference" devices. In this way, an emission intensity comparison can be used to gauge the amount of each mycotoxin in the sample detector tube, and, by applying appropriate calculations, the absolute amount of each mycotoxin in the original sample may be determined.

Alternatively, the fluorescence of the bands of the sample-developed detector tube may be compared to the fluorescence of a "reference guide" comprising fluorescent materials other than mycotoxins to gauge the level of each mycotoxin. Such a reference guide may conveniently be a card or other support on which a fluorescent compound is contained at varying levels corresponding to known quantities of the mycotoxins of interest. Thus, the fluorescence of each band of the detector tube could be matched to a level of fluorescence on the reference guide. A value would be assigned to each level allowing the calculation of the amount of mycotoxin in the original sample.

The developed detector tube could also be used in conjunction with an instrument capable of electronically detecting the fluorescent emission of each band of mycotoxin immobilized in the detector tube thereby providing a more exact quantitation of the fluorescence. Such as quantitation would allow the calculation of the level of each such mycotoxin the original sample. Such an instrument could also employ specific optical filters, monochromators, or the like to discriminate the wavelengths of the fluorescence detected. As will be appreciated by those skilled in the art, such discrimination would offer advantages in the specificity, sensitivity, and reproducibility of the assay.

EXAMPLE 3

Figure 3:
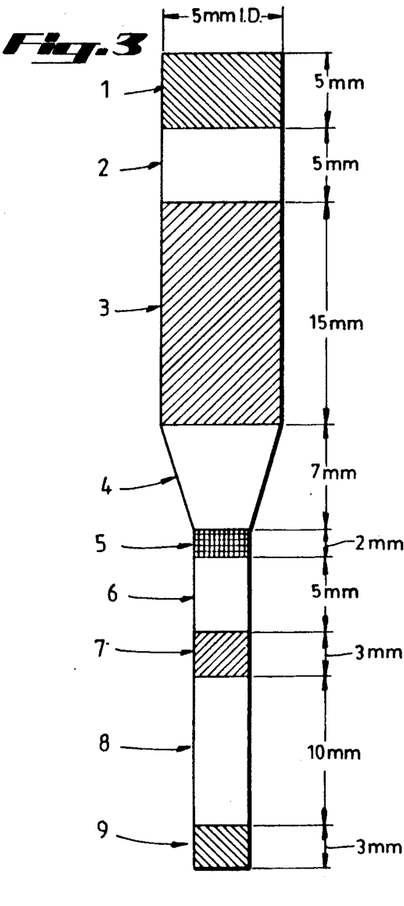
FIG. 3 is a cross-sectional view of a portion of the test devices disclosed in Examples 3 and 4.

This example illustrates how the invention may be employed to separate and detect zearalenone and aflatoxins in a sample potentially comprising a mixture of those mycotoxins as well as ochratoxin A. The particular detector tube illustrated employs pseudoboehmite to adsorb out ochratoxin A and other interfering compounds. A housing having sections of differing diameters is used to enhance effectiveness.

The packed portions of the detector tube is shown in cross section in FIG. 3. This device is designed to assay zearalenone and aflatoxins in a mixture of organic compounds extracted from feeds and foodstuffs. The design uses the same array of materials as that of Example 2, but the dimensions and preferred procedure for use are different.

The tube and the layers of packing material contained therein have the approximate dimensions shown in FIG. 3. The housing tube should have the properties described in Example 1. A Pasteur pipette may conveniently be used to provide the sections of differing diameters.

The nine layers of packing materials serve the same function as in Example 2 with the exception of layer 3 which is enlarged relative to its counterpart in the device of Example 2. The function of layer 3, which preferably comprises pseudoboehmite, is to immobilize ochratoxin A and other fluorescent compounds extracted from the sample which would otherwise bind downstream in the alumina layer (layer 5) or the Florisil ® layer (layer 7) and thereby interfere with the proper measurement of zearalenone or aflatoxins, respectively. Thus, this detector tube configuration allows for the specific detection/measurement of zearalenone and aflatoxins but not of ochratoxin A. The positioning of layer 3 in the larger diameter portion of the detector tube provides for a relatively greater quantity of adsorbant in that layer for the sample solution to contact—sufficient to immobilize substantially all ochratoxin A and other potential interfering organic compounds which may be present in the sample solution. A larger diameter layer of adsorbant is preferred to a thicker layer (as a way of providing a greater quantity of adsorbant in the detector tube) inasmuch as a thicker layer would reduce the flow rate of sample solution (or increase the pressure differential needed to maintain an acceptable flow rate) and is more susceptible to channeling and other flow-disturbing phenomena. The locating of layers 5 and 7 in the more narrow portion of the tube effects a greater sensitivity of detection of any zearalenone and/or aflatoxins, respectively, which become immobilized in the device upon development.

A preferred analytical procedure utilizing the detector tube described above is as follows:
1. 40 g of sample (e.g., corn, sorghum, peanuts, wheat, rice, soybeans) and 200 mL of 80% methanol in water (v/v) are placed in a blender and blended for 3 minutes at low speed.
2. Particulates are allowed to settle out and 5.5 mL of the clear supernatant liquid is transferred into a 20-mL glass screwcap vial through a coffee filter.
3. 6 mL of water are then added to the filter and collected in the same 20-mL vial.
4. 3 mL of toluene are then added to the solution in the vial; the cap is firmly affixed; and the vial inverted 20 times.
5. The vial is placed upright to allow the solvent phases to separate. The cap is then removed and 0.5 mL of extract is transferred to the top of the detector tube and allowed to drain into the packing material.
6. One mL of toluene/chloroform/acetone (95:20:5) is added to the top of the detector tube and allowed to flow through the packings. Positive pressure may be applied to the top of the device to increase the flow rate.
7. Using the procedure described in Example 2, the presence of zearalenone (about 100 ng) and/or aflatoxins (about 1 ng) in the sample is determined by examining for bright blue fluorescence in the appropriate layers.

EXAMPLE 4

This example illustrates the use of the selective adsorbants of the present invention to construct a detector tube for the detection and measurement of sterigmatocystin and aflatoxin $M_1$ in milk and milk products. Pseudoboehmite is employed to remove interfering compounds and Florisil ® and alumina are used to immobilize aflatoxins and sterigmatocystin. A tube housing having sections of differing internal diameters is used to enhance the sensitivity of the analysis.

Figure 4:
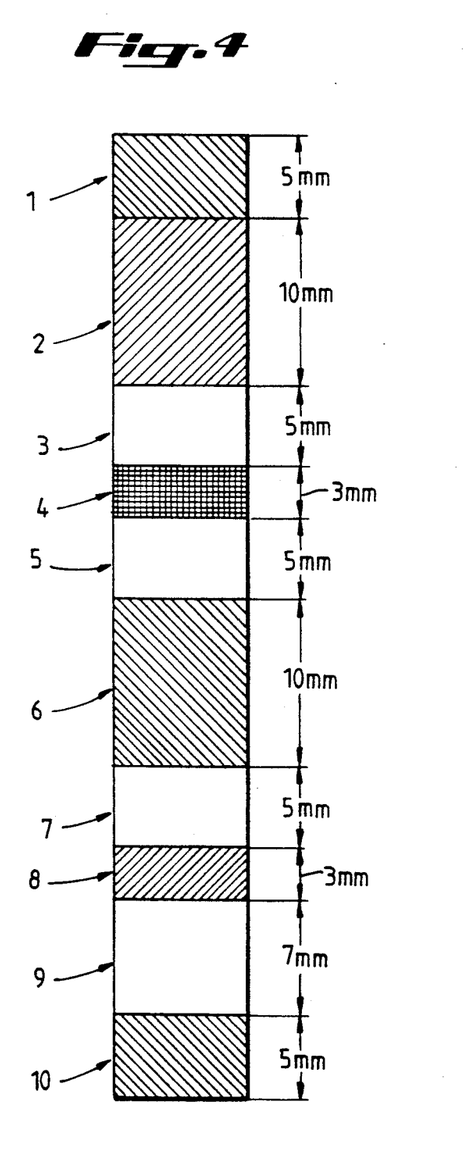
FIG. 4 is a cross-sectional view of a portion of a test device for the immobilization and detection of aflatoxins and deoxynivalenol which embodies the present invention.

The packed portion of the detector tube is illustrated in cross section in FIG. 4. The device is designed for the detection and semiquantitative determination of sterigmatocystin and aflatoxin M1 in a mixture of organic compounds extracted from milk or milk products. The tube housing preferable has the properties discussed in Example 1, above. Preferred approximate thicknesses for the various packing materials of the detector tube are indicated in FIG. 4.

Nine layers of materials are used to accomplish the specific resolution of sterigmatocystin and aflatoxin $M_1$. Materials other than the mycotoxin-selective adsorbants are employed to improve separation and detection. Layers 1 and 9 comprise cotton which layers act to maintain the integrity of the other layers during use, storage, and handling. Layers 2, 4, 6 and 8 are preferably sand. They function to physically separate the selective chemisorbants thereby enhancing discrimination of the fluorescent signals emanating from such layers when the analytes are immobilized therein. Other suitable materials for this purpose are discussed in Example 2.

The detector tube should have the properties described in Example 3. The purpose of layer 3, which preferably comprises pseudoboehmite, is to immobilize ochratoxin A and other fluorescent compounds extracted from the sample along with the analytes, which compounds would otherwise bind downstream to alumina (layer 5) or Florisil ® (layer 7) thereby interfering with the proper measurement of sterigmatocystin or aflatoxin $M_1$, respectively. Thus, this particular detector tube configuration permits the specific detection/measurement of sterigmatocystin and aflatoxins but not of ochratoxin A.

The locating of layer 3 in the large-diameter portion of the detector tube allows the sample to contact a larger amount of pseudoboehmite than would otherwise be possible. The actual amount should be sufficient to immobilize any and all ochratoxin A and other potentially interfering organic compounds which may be present in the sample.

The positioning of layers 5 and 7 in the more narrow portion of the tube effects a greater sensitivity of detection of any sterigmatocystin and/or aflatoxins, respectively, which are immobilized in these layers.

Layer 5 preferably comprises neutral alumina. Neutral alumina selectively adsorbs sterigmatocystin from the sample solution immobilizing it in the detector tube. Neutral alumina, however, allows other organic compounds including aflatoxin $M_1$ which might be present in the sample to pass through this layer to downstream layers. If sterigmatocystin is present in sufficient quantity to permit visual observation of its fluorescence, a bright yellow band in layer 5 will be seen when the detector tube is exposed to longwave uv radiation.

Layer 7 preferably comprises Florisil ® activated magnesium silicate. It selectively adsorbs aflatoxin $M_1$ from the sample solution, immobilizing it in that particular layer while allowing other organic compounds which might be in the sample to pass through. If aflatoxins are present in the sample in sufficient quantities to permit visual observation of their fluorescence, a bright blue band in layer 7 will be seen when the detector tube is exposed to longwave uv radiation.

The mycotoxin-selective detector tube described above allows samples of milk and milk products to be assayed for sterigmatocystin and aflatoxin $M_1$. The analysis is performed by dissolving the mycotoxins in a known volume of a solvent which will dissolve the mycotoxins and which also has the necessary properties to allow both mycotoxins and other potentially interfering compounds to bind to appropriate adsorbants as the sample solution contacts them.

For the analysis of mycotoxins in milk, the following procedure is preferred.

1. A fresh milk sample is mixed with an equal volume of hexane in a container suitable for the thorough mixing of the liquids. A syringe may conveniently be used for this purpose (e.g., 5 mL of milk plus 5 mL of hexane in a 20-mL syringe).
2. After mixing, the two liquid phases are allowed to separate. The aqueous phase (milk) will be the lower of the two.
3. The aqueous phase (milk) is drawn off (e.g., pushed out when the syringe is held with the opening pointed in the downward direction) and transferred to a screwcap vial.
4. Ethyl acetate is then added to the milk in the vial in a ratio of 2-to-1 (e.g., 10 mL of ethyl acetate for 5 mL milk). The vial is then capped and inverted ten times.
5. The phases are allowed to separate and a 2-mL aliquot of the upper phase is withdrawn and applied to the top of the detector tube and allowed to flow into the packings. One-half mL of ethyl acetate is added to the detector tube as a wash solvent to further develop the detector. Positive pressure may be applied to the top of the tube to increase the flow rate of sample through the tube.
6. The presence of sterigmatocystin (about 1 ng) is determined by examining for a bright yellow fluorescence in layer 5 using a longwave ultraviolet light source. The presence of aflatoxin $M_1$ (about 1 ng) is similarly determined by examining for a bright blue fluorescence in layer 7. The procedures described in Example 2 above are appropriate for this assay.

EXAMPLE 5

In this example, the novel adsorbants of the present invention are employed to construct a detector tube for the analysis of aflatoxins and deoxynivalenol (DON). Pseudoboehmite is used to remove ochratoxin A and other potentially interfering compounds. Alumina is used to immobilize DON and heat is used to provide enhanced levels of fluorescence, thereby lowering the detection limit of the determination. Florisil ® is used to selectively bind aflatoxins. The combined use of Florisil ® and alumina permits the resolution and separate detection of aflatoxins and DON.

The packed portion of a detector tube for the determination of aflatoxins and DON in a sample comprising a mixture of mycotoxins and other organic compounds is shown in cross section in FIG. 4. The tube itself preferably has the properties discussed in Example 1, above. The approximate preferred thicknesses of the various layers of packing materials within the detector tube are indicated in the figure.

Ten layers of materials are used to accomplish the specific resolution of the two mycotoxins of interest. Materials other than the chemisorbants selective for the two mycotoxins are included to improve the separation and detection. Layers 1 and 9 preferably comprise cotton. These layers function to maintain the physical integrity of the other layers during use, storage and handling. Layer 1 acts additionally to filter out particulates.

Layers 3, 5, 7, and 9 are sand. They are employed to physically separate the selective adsorbants thereby enhancing differentiation of the fluorescence of the mycotoxins immobilized in those chemisorptive layers. Other suitable materials for this purpose are discussed in Example 2, above.

Layer 2 is a preferably a mixture comprising sepiolite and halloysite. Sepiolite (or "meerschaum") is a mineral a mineral $Mg_3Si_4O_{10}(OH)_2.4H_2O$ consisting of a hydrous magnesium silicate that is an extremely light fine soft white clay dug chiefly in Asia Minor. Halloysite is a clay mineral $Al_2Si_2O_5(OH)_4.nH_2O$ occurring in soft white or light-colored masses and in at least 2 states of hydration—n=2 and n=4. The purpose of this layer is to immobilize fluorescent compounds other than aflatoxins and DON which may be in the sample which would otherwise bind downstream in the Florisil ® layer (layer 4) or the alumina layer (layer 8), thus interfering with the detection/measurement of aflatoxins and DON, respectively. Any other materials which bind the interfering compounds and not aflatoxins or DON could be substituted for or used in addition to sepiolite and halloysite in this layer.

Layer 4 preferably comprises Florisil ®. It selectively adsorbs aflatoxins from the mixture while allowing DON to passes through to downstream layers in the detector tube. If aflatoxins are present in the sample in sufficient quantity to permit visual observation of their fluorescence (at least about 2-5 ng), a bright blue band in layer 4 will be observed when the detector tube is exposed to longwave uv radiation.

Layer 6 preferably comprises charcoal. Its purpose is to immobilize fluorescent compounds other than DON which might bind in the downstream alumina layer (layer 8), thus interfering with the detection/measurement of DON. Any other materials which bind the interfering compounds and not DON could be substituted for or used in conjunction with charcoal in this layer.

Layer 8 preferably comprises neutral alumina. It selectively adsorbs DON from the sample solution but allows other classes of organic compounds which might be in the sample solution to pass through the layer. If DON is present in the sample in sufficient quantity (about 300 ng), upon heating the detector tube (e.g., 120° C. for 5 min.), a bright blue band in layer 8 will be observed when the device is exposed to longwave uv radiation. Any other material which binds DON (e.g., pseudoboehmite) could be substituted for neutral alumina in this layer. The adsorbant may be treated with an acidic substance such as aluminum chloride or oxalic acid to enhance the fluorescence of bound DON.

It is important that the Florisil ® layer be upstream from the layers used to bind DON and interfering compounds if aflatoxins are capable of binding to those layers (as is the case where aflatoxins bind to charcoal). Therefore, if the relative positions of the selective adsorbants were in any different order, separation of the mycotoxins from each other and from interfering compounds would not occur.

The detector tube described in this example allows the analysis of the mycotoxins indicated. These mycotoxins often contaminate grains, nuts and other feeds and food commodities.

The analysis may be accomplished by dissolving the mycotoxins in a known volume of an organic solvent having the properties of being able to dissolve aflatoxins and DON and possessing the appropriate characteristics to allow the mycotoxins to bind to the selective adsorbants when the sample solution contacts them in the detector tube. Examples of appropriate solvents are ethyl acetate, acetone, toluene and various combinations of these.

The sample solution is applied to the top of the detector tube (e.g., one mL or less) and is allowed to flow into the packing material. The device is further developed by adding a volume (e.g., one mL) of the same solvent as a wash solvent which is also allowed to flow through the various packings. Differential pressure may be applied to the tube to increase the rate of flow.

After such development, the detector tube containing immobilized mycotoxins is heated to effect an enhancement of fluorescence; for example, in an oven at 120° C. for 5 minutes. The device is then examined under longwave uv radiation. If present in the extract above the detection limit (above about 5 ng), aflatoxins will be observed as a bright blue fluorescent band in layer 4. Similarly, deoxynivalenol (if present in an amount greater than about 300 ng) will appear as a bright blue fluorescent band in layer 8. Additional methods for determining the quantity of the mycotoxins at this stage of the procedure are described in Example 2.

EXAMPLE 6

Described in this example are a detector tube and method for the assay of feeds and other foodstuffs for sterigmatocystin. In the device described, alumina or pseudoboehmite is used to immobilize the mycotoxin of interest (sterigmatocystin) thereby permitting its separation and detection in a mixture of organic compounds including other mycotoxins.

Figure 5:
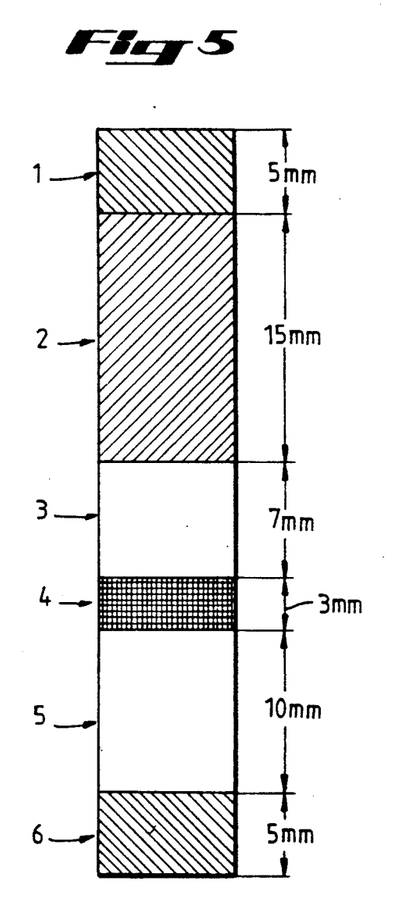
FIG. 5 is a cross-sectional view of a portion of the test devices disclosed in Examples 6, 7, 8, and 9.

The packed portion of the detector tube for the assay of sterigmatocystin is shown in cross section in FIG. 5. The tube itself preferably has the properties discussed in Example 1. Preferred approximate dimensions for the various packing materials are indicated in the figure.

In the detector tube shown, six layers of packing materials are employed to accomplish the specific resolution of sterigmatocystin. Materials other than the selective chemisorbants are included to improve the separation and detection. Layers 1 and 6 are preferably cotton. These layers function to maintain the integrity of the other layers during use, storage and handling. Layers 3 and 5 are preferably sand. These layers physically separate the selective chemisorbant layers thereby enhancing discrimination of the fluorescent emission of sterigmatocystin immobilized in the selective adsorbant. Other suitable packing materials for these layers are discussed in Example 2, above.

Layer 2 preferably comprises halloysite. It immobilizes chemicals in the sample solution which would otherwise bind in the downstream alumina layer (layer 4) and interfere with the accurate measurement of sterigmatocystin. Any other packing materials which bind interfering chemicals and not sterigmatocystin could be substituted for, or used in addition to halloysite in this layer of the device.

Layer 4 preferably comprises neutral alumina. Neutral alumina (as does acidic and basic alumina) selectively binds sterigmatocystin in the sample solution while allowing other organic chemicals to be transported through this layer. If sterigmatocystin is present in the sample solution in sufficient quantity to permit visualization of its fluorescence (approximately 2-5 ng), a bright yellow band in layer 4 will be observed when the detector tube is examined under longwave uv light. Any other material which binds sterigmatocystin and permits its fluorescence to be observed could be substituted for the neutral alumina in this layer. Specifically, pseudoboehmite or bayerite could be substituted as the selective adsorbant in this layer of the detector tube.

The detector tube disclosed in this example permits one to analyze for sterigmatocystin in feed and foods. The analysis is accomplished by dissolving the mycotoxin in a known volume of an organic solvent having the properties of being able to dissolve sterigmatocystin while allowing that mycotoxin to bind to the selective adsorbant in the detector tube when the sample solution is transported through that layer. Examples of appropriate solvents are acetone, ethyl acetate, methanol and toluene.

The sample solution is applied to the top of the detector tube (e.g., one mL or less) and allowed to flow through the device. The column is preferably further developed by adding a volume (e.g., one mL) of the same solvent as a wash solvent which is also allowed to flow through the tube. Differential pressure may be applied to the detector tube to increase the flow rate of sample solution and wash solvent. This may be conveniently accomplished by simply attaching a pipette bulb to the top of the tube and then squeezing the bulb.

Following development, the detector tube is examined under a longwave uv lamp preferably having an emission maximum at around 365 nm. If present in the sample in sufficient quantity, sterigmatocystin will be detected as a bright yellow fluorescence in layer 4. Suitable methods for determining or estimating the quantity of the mycotoxin are described in Example 2.

EXAMPLE 7

Described in this example are a detector tube and associated method for the assay of patulin in various fruits, fruit juices, and other commodities. Alumina is employed in the device described to selectively immobilize patulin thereby permitting its detection and/or measurement.

The packed portion of the detector tube for the assay of patulin is shown in cross section in FIG. 5. The tube itself preferably has the properties discussed in Example 1. Preferred approximate dimensions for the various packing materials are indicated in the figure.

In this detector tube, six layers of packing material are used to accomplish the specific resolution of patulin. Materials other than the selective adsorbants are included to enhance the separation and detection. Layers 1 and 6 are preferably cotton. These layers function to maintain the integrity of the other layers in the device during use, storage and handling. Layers 3 and 5 are preferably sand. They are used to physically separate the selective chemisorbant layer thereby enhancing discrimination of the fluorescence of the immobilized mycotoxin. Other suitable materials which may be employed in these layers are discussed in Example 2, above.

Layer 2 preferably comprises a mixture of neutral alumina and pseudoboehmite (1:1 by volume). The purpose of this layer is to immobilize chemicals in the sample solution which would otherwise bind downstream in the alumina layer (layer 4) and interfere with the accurate measurement of patulin. Any other packing materials which bind the interfering chemicals and not patulin could be substituted for, or used in addition to alumina and pseudoboehmite in this layer of the device.

Layer 4 preferably comprises neutral alumina coated with oxalic acid. This material may be prepared by dissolving a quantity of oxalic acid equal to about 0.05 to about 0.5% of the weight of neutral alumina to be used in diethyl ether and mixing this solution with a slurry of neutral alumina. The ether is subsequently removed by evaporation under vacuum. The alumina so treated is then activated by heating in a vacuum oven at about 50° to 100° C. for about 4 to 6 hours. It is contemplated that any other nonvolatile acids having pKa's less than about 3 may be used in place of oxalic acid (e.g., trichloroacetic acid). Patulin, which binds to the acid-treated alumina, will fluoresce blue when exposed to longwave uv radiation after being heated at about 120° C. for 5 minutes. Silica gel may be used in place of neutral alumina in this procedure.

The detector tube described above can be used for the analysis of patulin in samples of fruits, fruit juices and other commodities. The analysis is performed by dissolving the mycotoxin in a known volume of an organic solvent which both dissolves the patulin and permits the patulin and any co-dissolved interfering compounds to bind to the appropriate adsorbants as the sample solution is transported through the detector tube. Effective solvents include ethyl acetate and toluene.

The sample solution is applied to the top of the detector tube (for example, one mL or less) and is allowed to flow into the packings of the device. Further development is accomplished by adding a volume (e.g., one mL) of the same solvent used to dissolve the mycotoxin to the tube as a wash or "transporting" solvent. This is allowed to flow through the tube. The flow rate may be increased by applying differential pressure to the tube.

After development, the column is heated to produce a fluorescent compound from any patulin immobilized in layer 4. The heating may be accomplished by placing the detector tube in an oven at about 120° C. for about 5 minutes. The tube is then examined under longwave uv radiation. If present in the sample solution above the detection limit, patulin (or its fluorescent product) will appear as a blue fluorescent band in layer 4. Additional methods for determining or quantitating the patulin at this point are discussed in Example 2, above.

EXAMPLE 8

A detector tube and associated method for the analysis of citrinin are described in this method. The device utilizes bayerite or pseudoboehmite to selectively adsorb and immobilize citrinin from a solution comprising citrinin and other organic compounds including other mycotoxins. The immobilization of citrinin permits its detection and/or measurement by observation of its fluorescence.

The packed portion of the detector tube for the assay of patulin is shown in cross section in FIG. 5. The tube itself preferably has the properties discussed in Example 1. Preferred approximate dimensions for the various packing materials are indicated in the figure.

In this detector tube, six layers of packing material are used to accomplish the specific resolution of citrinin. Materials other than the selective adsorbants are included to enhance the separation and detection. Layers 1 and 6 are preferably cotton. These layers function to maintain the integrity of the other layers in the device during use, storage and handling. Layers 3 and 5 are preferably sand. They are used to physically separate the selective chemisorbant layer thereby enhancing discrimination of the fluorescence of the immobilized mycotoxin. Other suitable materials which may be employed in these layers are discussed in Example 2, above.

Layer 2 preferably comprises sepiolite. It functions immobilize chemicals in the sample solution which would otherwise bind downstream in the pseudoboehmite layer (layer 4) and interfere with the measurement of citrinin. Any other packing material(s) which would bind interfering compounds and not citrinin could be substituted for or used in conjunction with the sepiolite in this layer of the device.

Layer 4 preferably comprises pseudoboehmite. It selectively adsorbs citrinin in the sample solution while allowing other dissolved compounds in the sample solution to be transported through this layer. If citrinin is present in the sample solution in sufficient quantity to permit observation of its fluorescence, a yellow-green band in layer 4 will be observed when the detector tube is exposed to longwave uv radiation. Any other material which selectively binds citrinin and allows observation of its fluorescence (e.g., bayerite or alumina) could be substituted for pseudoboehmite in this layer.

The detector tube described above allows one to conveniently analyze for citrinin in feeds and foodstuffs. The analysis may be performed by dissolving the mycotoxin in a known volume of an organic solvent which both effectively solubilizes the mycotoxin and allows it and other co-dissolved compounds to bind to the appropriate chemisorbants in the detector tube. Examples of appropriate solvents for this purpose are chloroform, acetone, toluene and ethyl acetate.

The sample solution is applied to the top of the detector tube (for example, one mL or less) and is allowed to flow into the packings of the device. Further development is accomplished by adding a volume (e.g., one mL) of the same solvent used to dissolve the mycotoxin to the top of the tube as a wash or "transporting" solvent. This is allowed to flow through the tube. The flow rate may be increased by applying positive pressure to the top of the column.

After such development, the detector tube is examined under a uv light source having an emission maximum at about 365 nm. If present in the sample solution in sufficient quantity, citrinin will be detected as a bright yellow-green fluorescence in layer 4. Methods for determining the quantity of the mycotoxin in the feed or food sample are discussed in Example 2, above.

EXAMPLE 9

A detector tube and associated method for the analysis of ergots are described in this method. The device utilizes alumina or silica gel to selectively adsorb and immobilize ergots from a solution comprising ergots and other organic compounds including other mycotoxins. The immobilization of ergots permits their detection and/or measurement by observation of their fluorescence.

The packed portion of the detector tube for the assay of ergots is shown in cross section in FIG. 5. The tube itself preferably has the properties discussed in Example 1. Preferred approximate dimensions for the various packing materials are indicated in the figure.

In this detector tube, six layers of packing material are used to accomplish the specific resolution of ergots. Materials other than the selective adsorbants are included to enhance the separation and detection. Layers 1 and 6 are preferably cotton. These layers function to maintain the integrity of the other layers in the device during use, storage and handling. Layers 3 and 5 are preferably sand. They are used to physically separate the selective chemisorbant layer thereby enhancing discrimination of the fluorescence of the immobilized mycotoxin. Other suitable materials which may be employed in these layers are discussed in Example 2, above.

Layer 2 preferably comprises the natural zeolite mordenite [Chemical Abstracts Service Registry numbers 12445-20-4 and 12173-98-7]. It functions to immobilize chemicals in the sample solution which would otherwise bind downstream in the alumina layer (layer 4) and interfere with the measurement of ergots. Any other packing material(s) which would bind interfering compounds and not ergots could be substituted for or used in conjunction with the zeolite in this layer of the device.

Layer 4 preferably comprises acidic alumina. It selectively adsorbs ergots in the sample solution while allowing other co-extracted organic compounds to pass through the layer. If ergots are present in the sample solution in sufficient quantities to permit observation of their fluorescence, a blue band will be observed when the detector tube is exposed to longwave uv radiation. Any other material which selectively binds ergots and permits observation of their fluorescence could be substituted in this layer of the device.

The detector tube described above allows one to conveniently and rapidly analyze feeds and foodstuffs for ergot contamination. The analysis is performed by dissolving the mycotoxins (e.g., ergotamine) in a known volume of an organic solvent which both effectively solubilizes the mycotoxin(s) and allows it and other codissolved compounds to bind to the appropriate chemisorbants in the detector tube. Examples of appropriate solvents for this purpose are chloroform, acetone, and ethyl acetate.

The sample solution is applied to the top of the detector tube (for example, one mL or less) and is allowed to flow into the packings of the device. Further development is accomplished by adding a volume (e.g., one mL) of the same solvent used to dissolve the mycotoxin to the top of the tube as a wash or "transporting" solvent. This is allowed to flow through the tube. The flow rate may be increased by applying positive pressure to the top of the column.

After such development, the detector tube is examined under a uv light source having an emission maximum at about 365 nm. If present in the sample solution in sufficient quantity, the ergot(s) will be detected as a blue fluorescence in layer 4. Methods for determining the quantity of the mycotoxin in the feed or food sample are discussed in Example 2, above.

The foregoing description has been directed to particular embodiments of the invention in accordance with the requirements of the United States patent statutes for the purposes of illustration and explanation. It will be apparent to those skilled in this art, however, that many modifications and changes in the compositions, devices, and methods set forth will be possible without departing from the scope and spirit of the invention. It is intended that the following claims be interpreted to embrace all such modifications and changes.

What is claimed is:

1. An apparatus for selective separation and detection of a mycotoxin from a solution which may contain interfering materials comprising:

a transparent tube containing a sequence of discrete layers including:
(1) A first adsorbent layer which is capable of selectively binding interfering materials from the solution as it passes through the tube;
(2) A second adsorbent layer having a structure-selective affinity for a mycotoxin said second adsorbent layer being capable of immobilizing said mycotoxin in the presence of an appropriate solvent; and
(3) A support layer between the first and second adsorbent layers;
said support layer being made of material other than those of said first and second adsorbent layers.

2. The apparatus of claim 1 wherein said first adsorbent layer comprises sepiolite, halloysite, mordenite, activated magnesium silicate, silica gel, or mixtures thereof; said support layer comprises diatomaceous earth, glass wool, a silicate, carbon, sulfur, iron filings, an aluminosilicate, cellulose fiber, sand, or mixtures thereof; said second adsorbent layer comprises pseudo-boehmite, bayerite, gibbsite, boehmite, bauxite, alumina, or mixtures thereof and is selective for a mycotoxin selected from the group consisting of zearalenone, ochratoxin A, and citrinin.

3. The apparatus of claim 1 wherein said first adsorbent layer comprises pseudoboehmite, bayerite, gibbsite, boehmite, bauxite, alumina, or mixtures thereof; said support layer comprises diatomaceous earth, glass wool, a silicate, carbon, sulfur, iron filings, an aluminosilicate, cellulose fiber, sand, or mixtures thereof; said second adsorbent layer comprises activated magnesium silicate and is selective for a mycotoxin selected from the group consisting of aflatoxin and aflatoxin-M1.

4. The apparatus of claim 1 wherein said second adsorbent layer is selective for a mycotoxin selected from the group consisting of deoxynivalenol, sterigmatocystin, patulin and ergot.

5. Apparatus for the separation and detection of aflatoxin and ochratoxin A from a solution which comprises:
   a transparent tube containing a sequence of discrete layers including:
   (1) A first adsorbent layer having a structure-selective affinity for ochratoxin A, but not aflatoxin;
   (2) A second adsorbent layer having a structure-selective affinity for aflatoxin; and
   (3) A support layer between the first and second adsorbent layers;
   said support layer being made of material other than those of said first and second adsorbent layers.

6. The apparatus of claim 5 wherein said first adsorbent layer comprises pseudoboehmite, bayerite, gibbsite, boehmite, bauxite, alumina having activity grade IV or V, or mixtures thereof; said support layer comprises diatomaceous earth, glass wool, a silicate, carbon, sulfur, iron filings, an aluminosilicate, cellulose fiber, sand, or mixtures thereof; and said second adsorbent layer comprises activated magnesium silicate.

7. The apparatus of claim 5 wherein said first adsorbent layer comprises bayerite, said support layer comprises diatomaceous earth, and said second adsorbent layer comprises activated magnesium silicate.

8. Apparatus for the separation and detection of ochratoxin A, zearalenone, and aflatoxin from a solution which comprises:
   a transparent tube containing a sequence of discrete layers including:
   (1) A first adsorbent layer having a structure-selective affinity for ochralayer A, but not zearalenone or aflatoxin;
   (2) A second adsorbent layer having a structure-selective affinity for zearalenone, but not aflatoxin;
   (3) A third adsorbent layer having a structure-selective affinity for aflatoxin;
   (4) A first support layer between the first and second adsorbent layers;
   said first support layer being made of material other than those of said first, second and third adsorbent layers; and
   (5) A second support layer between the second and third adsorbent layers;
   said second support layer being made of material other than those of said first, second and third adsorbent layers.

9. The apparatus of claim 8 wherein said first adsorbent layer comprises pseudoboehmite; said first and second support layers comprise diatomaceous earth, glass wool, a silicate, carbon, sulfur, iron filings, an aluminosilicate, cellulose fiber, sand, or mixtures thereof; said second adsorbent layer comprises neutral alumina; and said third adsorbent layer comprises activated magnesium silicate.

10. An apparatus for the separation and detection of zearalenone and aflatoxin from a solution which comprises:
    a transparent tube containing a sequence of discrete layers including:
    (1) A first adsorbent layer having a structure-selective affinity for zearalenone, but not aflatoxin, said first adsorbent being capable of immobilizing said zearalenone in the presence of an appropriate solvent, but not aflatoxin;
    (2) A second adsorbent layer having a structure-selective affinity for aflatoxin, said second adsorbent layer being capable of immobilizing said aflatoxin in the presence of an appropriate solvent;
    (3) A first support layer between the first and second adsorbent layers;
    said first support layer being made of material other than those of said first and second adsorbent layers.

11. The apparatus of claim 10 wherein said solution may contain interfering materials which further comprises:
    (1) A third adsorbent layer which is capable of selectively binding interfering materials from the solution as it passes through the tube located prior to said first adsorbent layer; and
    (2) A second support layer between the third and first adsorbent layers;
    said second support layer being made of material other than those of said first, second and third adsorbent layers.

12. The apparatus of claim 11 wherein said third adsorbent layer comprises pseudoboehmite; said first and second support layers comprise diatomaceous earth, glass wool, a silicate, carbon, sulfur, iron filings, an aluminosilicate, cellulose fiber, sand, or mixtures thereof; said first adsorbent layer comprises neutral alumina; and said second adsorbent layer comprises activated magnesium silicate.

13. Apparatus for the separation and detection of sterigmatocystin and aflatoxin-M1 which comprises:
    a transparent tube containing a sequence of discrete layers including:
    (1) A first adsorbent layer having a structure-selective affinity for sterigmatocystin, but not aflatoxin-M1;
    (2) A second adsorbent layer having a structure-selective affinity for aflatoxin-M1; and
    (3) A first support layer between the first and second adsorbent layers;
    said first support layer being made of material other than those of said first and second adsorbent layers.

14. The apparatus of claim 13 wherein said solution may contain interfering materials which further comprises:
    (1) A third adsorbent layer which is capable of selectively binding interfering materials from the solution as it passes through the tube located prior to said first adsorbent layer; and
    (2) A second support layer between said third and first adsorbent layers;

said second support layer being made of material other than those of said first, second and third adsorbent layers;

15. The apparatus of claim 14 wherein said third adsorbent layer comprises pseudoboehmite; said first and second support layers comprise diatomaceous earth, glass wool, a silicate, carbon, sulfur, iron filings, an aluminosilicate, cellulose fiber, sand, or mixtures thereof; said first adsorbent layer comprises neutral alumina; and said second adsorbent layer comprises activated magnesium silicate.

16. Apparatus for the separation and detection of aflatoxin and deoxynivalenol from a solution which comprises:
   a transparent tube containing a sequence of discrete layers including:
   (1) A first adsorbent layer having a structure-selective affinity for aflatoxin, but not deoxynivalenol;
   (2) A second adsorbent layer having a structure-selective affinity for deoxynivalenol; and (3) A first support layer between the first and second adsorbent layers;

said first support layer being made of material other than those of said first and second adsorbent layers.

17. The apparatus of claim 16 wherein said solution may contain interfering materials which further comprises:

(1) A third adsorbent layer which is capable of selectively binding interfering materials from the solution as it passes through the tube located prior to said first adsorbent layer; and (2) A second support layer between the third and first adsorent layers;

said second support layer being made of material other than those of said first, second and third adsorbent layers.

18. The apparatus of claim 17 wherein said third adsorbent layer comprises halloysite, sepiolite, or mixtures thereof; said first and second support layers comprise diatomaceous earth, glass wool, a silicate, carbon, sulfur, iron filings, an aluminosilicate, cellulose fiber, sand, or mixtures thereof; said first adsorbent layer comprises activated magnesium silicate; and said second adsorbent layer comprises neutral alumina.

19. Apparatus for the separation and detection of sterigmatocystin from a solution which may contain interfering materials comprising:

a transparent tube containing a sequence of discrete layers including:

(1) A first adsorbent layer which is capable of selectively binding interfering materials from the solution as it passes through the tube;

(2) A second adsorbent layer having a structure-selective affinity for sterigmatocystin; and (3) A support layer between said first and second adsorbent layers;

said support layer being made of material other than those of said first and second adsorbent layers.

20. The apparatus of claim 19 wherein said first adsorbent layer comprises halloysite, said support layer comprises diatomaceous earth, glass wool, a silicate, carbon, sulfur, iron filings, an aluminosilicate, cellulose fiber, sand, or mixtures thereof; and said second adsorbent layer comprises neutral alumina, pseudoboehmite, or bayerite.

21. Apparatus for separation and detection of patulin from a solution which may contain interfering materials comprising:

a transparent tube containing a sequence of discrete layers including:

(1) A first adsorbent layer which is capable of selectively binding interfering materials from the solution as it passes through the tube;

(2) A second adsorbent layer having a structure-selective affinity for patulin; and (3) A support layer between the first and second adsorbent layers;

said support layer being made of material other than those of said first and second adsorbent layers.

22. The apparatus of claim 21 wherein said first adsorbent layer comprises a mixture of neutral alumina and pseudoboehmite; said support layer comprises diatomaceous earth, glass wool, a silicate, carbon, sulfur, iron filings, an aluminosilicate, cellulose fiber, sand, or mixtures thereof; and said second adsorbent layer comprises neutral alumina coated with oxalic acid or silica gel coated with oxalic acid.

23. Apparatus for separation and detection of citrinin from a solution which may contain interfering materials comprising:

a transparent tube containing a sequence of discrete layers including:

(1) A first adsorbent layer which is capable of selectively binding interfering materials from the solution as it passes through the tube;

(2) A second adsorbent layer having a structure-selective affinity for citrinin; and (3) A support layer between the first and second adsorbent layers;

said support layer being made of material other than those of said first and second adsorbent layers.

24. The apparatus of claim 23 wherein said first adsorbent layer comprises sepiolite; said support layer comprises diatomaceous earth, glass wool, a silicate, carbon, sulfur, iron filings, an aluminosilicate, cellulose fiber, sand, or mixtures thereof; and said second adsorbent layer comprises pseudoboehmite.

25. Apparatus for separation and detection of ergots from a solution which may contain interfering materials comprising:

a transparent tube containing a sequence of discrete layers including:

(1) A first adsorbent layer which is capable of selectively binding interfering materials from the solution as it passes through the tube;

(2) A second adsorbent layer having a structure-selective affinity for ergots; and (3) A support layer between the first and second adsorbent layers;

said support layer being made of material other than those of said first and second adsorbent layers.

26. The apparatus of claim 25 wherein said first adsorbent layer comprises mordenite; said support layer comprises diatomaceous earth, glass wool, a silicate, carbon, sulfur, iron filings, an aluminosilicate, cellulose fiber, sand, or mixtures thereof; and said second adsorbent layer comprises acidic alumina.

27. A kit for selective separation and detection of a mycotoxin from a solution which may contain interfering materials comprising:

a transparent tube containing a sequence of discrete layers including:

(1) A first adsorbent layer which is capable of selectively binding interfering materials from the solution as it passes through the tube;

(2) A second adsorbent layer having a structure-selective affinity for a mycotoxin said second adsorbent layer being capable of immobilizing said mycotoxin in the presence of an appropriate solvent;

(3) A support layer between the first and second adsorbent layers;

said support layer being made of material other than those of said first and second adsorbent layers; and an appropriate solvent.

28. The kit of claim 27 wherein the second adsorbent layer comprises activated magnesium silicate.

29. The kit of claim 27 wherein the appropriate solvent comprises toluene.

30. A kit for the separation and detection of zearalenone and aflatoxin from a solution comprising:

a transparent tube containing a sequence of discrete layers including:

(1) A first adsorbent layer having a structure-selectively affinity for zearalenone, but not aflatoxin, said first adsorbent being capable of immobilizing said zearalenone in the presence of an appropriate solvent, but not aflatoxin;

(2) A second adsorbent layer having a structure-selective affinity for aflatoxin, said second adsorbent layer being capable of immobilizing said aflatoxin in the presence of an appropriate solvent;

(3) A first support layer between the first and second adsorbent layers;

said first support layer being made of material other than those of said first and second adsorbent layers; and an appropriate solvent.

31. The kit of claim 30 wherein the first adsorbent layer comprises neutral alumina and the second adsorbent layer comprises magnesium silicate.

32. The kit of claim 30 wherein the appropriate solvent comprises toluene.

* * * * *

UNITED STATES PATENT AND TRADEMARK OFFICE
CERTIFICATE OF CORRECTION

PATENT NO. : 5,178,832
DATED : Jan. 12, 1993
INVENTOR(S) : Timothy D. Phillips, et al It is certified that error appears in the above-indentified patent and that said Letters Patent is hereby corrected as shown below:

On title page, item [75] the addresses of "William C. Gordon and Linda J. Gordon" should read as follows:

--both of Stillwater, Minnesota--

In column 25, line 48, please delete "ochralayer" and insert therefor --ochratoxin--.

In column 27, line 35, please delete "adsorent" and insert therefor --adsorbent--.

Signed and Sealed this

Twenty-fourth Day of May, 1994

BRUCE LEHMAN

Attest:

Attesting Officer

Commissioner of Patents and Trademarks